United States Patent [19]

Stoll

[11] Patent Number: 4,646,573

[45] Date of Patent: Mar. 3, 1987

[54] SCANNING ACOUSTIC MICROSCOPE

[75] Inventor: Erich P. Stoll, Stallikon, Switzerland

[73] Assignee: International Business Machines Corporation, Armonk, N.Y.

[21] Appl. No.: 841,496

[22] Filed: Mar. 19, 1986

[30] Foreign Application Priority Data

Apr. 26, 1985 [EP] European Pat. Off. ....... 8510515909

[51] Int. Cl.⁴ .......................................... G01N 29/00
[52] U.S. Cl. ........................................ 73/606; 73/642
[58] Field of Search ........................ 73/606, 642, 644

[56] References Cited

U.S. PATENT DOCUMENTS

| | | | |
|---|---|---|---|
| 3,934,460 | 1/1976 | Sherwin et al. | 73/642 |
| 4,151,752 | 5/1979 | Perdijon | 73/642 |
| 4,487,069 | 12/1984 | Ishikawa et al. | 73/606 |
| 4,491,020 | 1/1985 | Chubachi | 73/606 |
| 4,541,281 | 9/1985 | Chubachi et al. | 73/606 |
| 4,587,848 | 5/1986 | Nakamura et al. | 73/606 |

Primary Examiner—Anthony V. Ciarlante
Attorney, Agent, or Firm—Terry J. Ilardi

[57] ABSTRACT

The disclosed scanning acoustic microscope comprises a solid lens body consisting of two sections of materials having different sound propagation characteristics but matching acoustic impedances. A lens is formed by the interface of said two sections and has a focal point coinciding with the apex of a sharply pointed tip formed at the free surface of one of said sections. The tip and the specimen to be investigated are immersed in a coupling medium having a relatively high acoustic absorption coefficient. The lens body carries an acoustic transducer on its surface remote from the tip for sending plane sound waves through the lens and tip onto the specimen. Acoustic waves reflected from the specimen are also received by this transducer. Acoustic waves transmitted through the specimen optionally may be received by a transducer arranged on the opposite side of the specimen. By appropriate processing of the received signals, high-resolution (10 nm) images of the specimen can be obtained.

11 Claims, 2 Drawing Figures

SCANNING ACOUSTIC MICROSCOPE

FIELD OF THE INVENTION

This invention relates to scanning acoustic microscopes in which a beam of acoustic energy is used to obtain information about the surface region of a specimen, down to a certain penetration depth, and with a resolution comparable to, or better than, the resolution of optical microscopes.

BACKGROUND OF THE INVENTION

Scanning acoustic microscopes are known in the art. After an initial effort disclosed by S. Sokolov in "An Ultrasonic Microscope," Dokl. Akad. Nauk., Vol. 64, pp. 333–335 (1949), the first demonstrated scanning acoustic microscope was described by R. A. Lemons and C. F. Quate in "Acoustic Microscopy by Mechanical Scanning," Appl. Phys. Letters, Vol. 24, pp. 163–164 (1974). A microscope using sound rather than light has two main advantages. First, the images are formed from information obtained by the interaction of sound waves with the specimen and, thus, contrast in acoustically generated images relates to the mechanical properties of the specimen. Actually, specimens which appear uniform or opaque under an optical microscope can produce a high contrast image when inspected with an acoustic microscope. Second, the spatial resolution of an imaging system depends on the wavelength of the illuminating radiation. In an optical microscope the greatest resolution is about 0.3 $\mu$m in green light. Since the speed of sound wave propagation is very much less than the speed of light, only modest acoustic frequencies are necessary to obtain comparable acoustic wavelengths. Accordingly, an acoustic microscope has a potential for five to ten times better resolution than the optical limit.

The principles and the design of conventional acoustic microscopes have been extensively discussed in the literature, e.g. in V. Jipson and C. F. Quate, "Acoustic Microscopy at Optical Wavelengths," Appl. Phys. Letters, Vol. 32, pp. 789–791 (1978); J. E. Heiserman, "Cryogenic Acoustic Microscopy: The Search for Ultrahigh Resolution Using Cryogenic Liquids," Physica, Vols. 109 & 110B, pp. 1978–1989 (1982); and D. A. Sinclair, I. R. Smith and H. K. Wickramasinghe, "Recent Developments in Scanning Acoustic Microscopy," The Radio and Electronic Engineer, Vol. 52., No. 10, pp. 479–493 (1982).

Briefly, in a conventional scanning acoustic microscope, the specimen is translated point-by-point and line-by-line in a raster pattern past a focused diffraction-limited acoustic beam. The beam is generated by a piezoelectric transducer attached to the rear surface of a sapphire disk and centered on the axis of a single-surface spherical lens ground into the sapphire surface opposite the transducer. The specimen is translated in the focal plane of the lens, which is usually coated with an antireflection glass layer of one-quarter wavelength thickness. The lens and specimen are immersed in a body of liquid, such as water. The acoustic beam travelling down the sapphire is focused onto the specimen where it gets reflected and detected by the piezoelectric transducer. An electronic circulator serves to discriminate the reflected signal from the input signal. The output signal is used to modulate the brightness of a cathode ray tube display, whose x and y axes are synchronized with the scanning of the specimen. In order to produce acoustic wavelengths in the coupling liquid of less than a micrometer, the transducer is driven at frequencies in the gigahertz range. FIG. 1, published in several of the references cited above, shows the basic components of a prior art scanning acoustic microscope.

As already pointed out by P. Sulewski, D. J. Bishop and R. C. Dynes in "A Description of the Bell Laboratories Scanned Acoustic Microscope," The Bell Syst. Tech. Journ., Vol. 61, No. 9, p. 2174 et seq. (1982), the theoretical resolution of the acoustic microscope is proportional to the wavelength. Thus, an increase in the frequency should improve the resolution. However, for water and many other liquids, the acoustic attenuation is proportional to the second power of the frequency so that increasing the frequency only dramatically increases the power losses within the coupling liquid. In the interest of preserving the signal-to-noise ratio at an acceptable level, frequencies in the range of 3 GHz are presently considered optimal.

The resolving power of the conventional acoustic microscope is also limited by problems related to the acoustic beam diameter, in other words, to the diameter of the lens used. The smallest lens diameter found reported in the literature is 20 $\mu$m (Sinclair et al., op. cit., p. 492). The resolution achievable with this lens was reported to be 220 nm at 1 GHz, with argon gas at 40 bar being used as the coupling medium.

A better resolution than is achievable with an optical microscope is not possible with a conventional acoustic microscope unless a monatomic gas at high pressure (such as argon) or a cryogenic liquid (such as liquid helium) is used as the coupling medium in place of water (Heiserman, op. cit.). While such a coupling medium will improving the resolution, it creates an ambient environment which restricts the use of the acoustic microscope to only the limited range of specimens suited for such an environment.

DISCLOSURE OF THE INVENTION

It is an object of the present invention to provide a new scanning acoustic microscope which permits a resolution on the order of 10 nm at an acceptable signal-to-noise ratio without imposing difficult environmental conditions on the specimen.

Accordingly, the described scanning acoustic microscope comprises: an acoustic lens formed in a solid body interfacing with a coupling medium in which a specimen to be inspected is immersed; at least one transducer for generating and detecting sound waves in said solid body; and means for raster-scanning the focal point of said lens across the specimen, the improvement being that said solid body is composed of a first section of a material having a first velocity of sound, and a second section of a material having a second velocity of sound lower than said first velocity of sound, that one transducer is fixed on the free surface of said first section of the solid body, and that said lens is formed at the interface between said first and second sections of the solid body, the focal point of said lens corresponding to a sharp tip formed at the surface of said second section remote from said lens, said tip being immersed in said coupling medium and being adapted to be raster-scanned with respect to said specimen.

BRIEF DESCRIPTION OF THE DRAWINGS

An embodiment of this invention will now be described by way of example with reference to the attached drawings, in which.

BEST MODE FOR CARRYING OUT THE INVENTION

Figure 1:
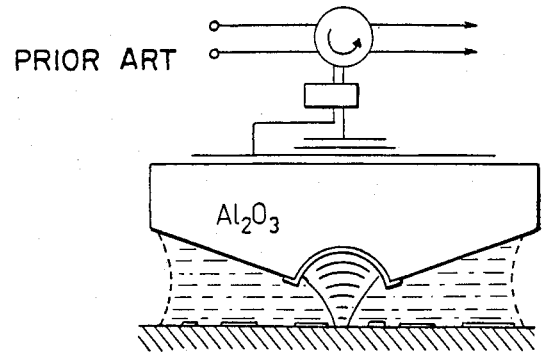
FIG. 1 shows a conventional scanning acoustic microscope.

FIG. 1 schematically shows a scanning acoustic microscope from the prior art designed to use a sound wave reflected by the specimen to form an image on a display screen. Under certain conditions it is possible to provide a second transducer underneath the specimen for detecting sound energy passing through the specimen, thus investigating the specimen in a transmission mode.

Figure 2:
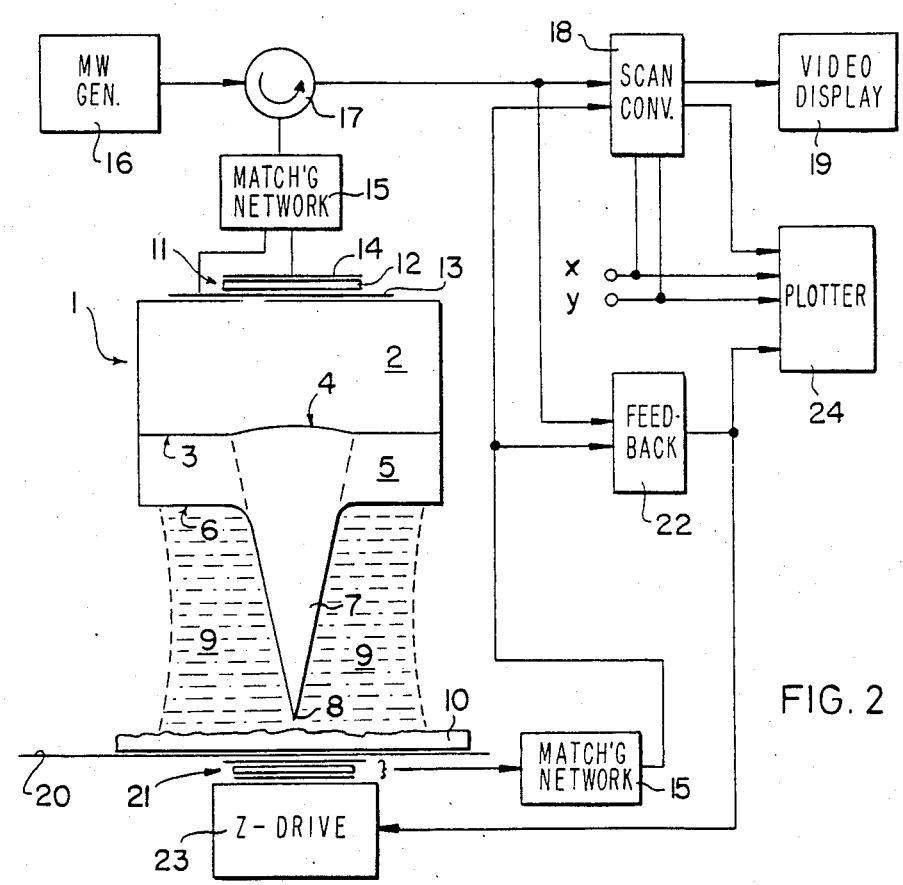
FIG. 2 shows a scanning acoustic microscope in accordance with the invention.

The basic limitations inherent in the conventional acoustic microscope, viz. the size of the beam diameter and the velocity ratio of the sound waves in the solid lens structure and the coupling medium, are circumvented with the novel design schematically shown in FIG. 2.

The lens body 1 consists of a first section 2 of a solid material having a relatively high velocity of sound, such as the usual sapphire. Ground into the lower surface 3 of the first section 2 is a single-surface lens 4 having a radius between 50 $\mu$m and 600 $\mu$m. Attached to the lower surface 3 is a second section 5 of a solid material having a velocity of sound lower than the material of section 2. Section 5 is shaped so as to match the contour of section 2, especially lens 4, so that there is no gap between sections 2 and 5 at the location of lens 4.

At the surface 6 of section 5 facing away from lens 4 there is provided a sharply pointed tip 7 which has its longitudinal axis aligned with the axis of lens 4. The shape of lens 4, the thickness of section 5 and the length of tip 7 are designed such that the focus of lens 4 falls onto the apex 8 of tip 7. The radius of the tip at its apex 8 preferably should be on the order of 10 nm.

On top of lens body 1 there is provided a piezoelectric transducer 11, which consists of a sputtered film 12 of zinc oxide between two films 13 and 14 of gold. Via an electrical matching network 15, the transducer is connected to a microwave generator 16. Transducers of this type are used extensively in a variety of microwave acoustic applications to convert electrical pulses having frequencies even exceeding 10 GHz into acoustic plane waves. In the arrangement of FIG. 2, the acoustic plane waves travel through the sapphire crystal 2 to the spherical lens 4 and on through the section 5 material into tip 7. The transducer 11 is also used to detect the acoustic wave reflected by the specimen and travelling back through tip 7 and sections 5 and 2 of lens body 1. The transducer then reconverts the reflected acoustic wave into a microwave. A circulator 17 is required for directing the input microwave to the transducer and for directing the output microwave to scan converter 18 for display purposes. Scan converter 18 uses the x and y positioning information together with the rectified output pulse of transducer 11 to construct a video picture on the screen of a video display unit 19.

If the acoustic microscope is to be operated in the transmission mode, the specimen 10 is supported on a thin polyester film 20. The acoustic radiation from tip 7 will then pass through the specimen and be collected by a second transducer 21, which is appropriately connected to scan converter 18. In this mode of operation, circulator 17 is not required.

As above mentioned, section 2 of lens body 1 consists of sapphire ($Al_2O_3$) with spherical lens 4 ground into its lower surface 3. To avoid undesirable reflections at the interface between section 2 and adjacent section 5, the sound velocity in sapphire times the density of sapphire should be essentially equal to the sound velocity of the material of section 5 times its density. This condition is sufficiently satisfied when section 5 is made of one of the common metals, such as steel, nickel, copper, silver, etc.

The manufacture of section 5 with its lens protrusion and the tip 7 must be carefully done. One possibility is to cast a low-melting point alloy onto the lower surface 3 of the sapphire to avoid any gap between the interface materials at the spherical surface of lens 4. Regions 2 and 5 may be joined together with a bolt and nut arrangement, or they may be glued together with a glue used to form optical elements, such as Canada balsam. If a gap occurs in the lens area, it could be filled with a droplet of mercury, but because of its smaller product of sound velocity and density, reflections may arise.

In contrast to prior art acoustic microscopes where a coupling fluid is used which has a small absorption coefficient in the acoustic frequency range of interest, the acoustic microscope of the present invention requires a coupling fluid with a large absorption coefficient in the acoustic frequency range of interest. Liquids such as benzene ($C_6H_6$) and carbon tetrachloride ($CCl_4$) may be used, but water can be used as well.

Due to the absorption characteristics of the coupling medium 9, the intensity of the reflected or transmitted sound waves strongly depends on the distance between tip 7 and the surface of specimen 10. If the relative separation between the specimen and tip is kept constant while the tip is scanned across the specimen, roughness in the surface of the specimen 10 will result in variations in the tip to surface distance, resulting in deviations in the amplitude of the reflected signal with respect to a nominal amplitude value. These deviations are supplied to a suitable feedback loop arrangement 22 for on-line and real-time adjustment of the tip to specimen distance through control of a z-drive module 23 to which the specimen is attached. The control signal from feedback unit 22 is also supplied to a plotter 24 together with the xy scanning signals. Since the specimen 10 is scanned in a matrix fashion, plotter 24 will draw an image of the topography of specimen 10 with a resolution of about 10 nm in the vertical direction. The resolution obtained in the xy direction depends upon the horizontal scanning means utilized. An integrated xyz drive module constructed of piezoelectric elements is known from the prior art which permits horizontal scanning steps in the nanometer range.

In operation in the reflection mode, an input pulse train is generated by microwave generator 16 at a frequency in the 3 to 10 GHz range. A pulsed wave is required to give circulator 17 the time needed for discriminating between input waves and reflected waves. The input wave passes through matching network 15 and excites transducer 11, which sends a plane sound wave into section 2 of lens body 1. This sound wave is focused by lens 4 into section 5, with the focal point falling onto the apex 8 of tip 7.

Following is a numerical example of suitable dimensions for the lens body of the invention. With a lens diameter of about 0.25 mm and a radius of curvature of about 1 mm, the focal length of the lens will be around 0.8 mm. About 0.5 mm of this distance is in the tip and about 0.3 mm is in section 5. The thickness of Section 2 above lens 4 may be 0.4 mm, for example. After the lens has been ground into section 2, which consists of $Al_2O_3$, the section 5 metal is cast using the lens-carrying surface 3 of section 2 as a mold to avoid gap formation in the lens area. Then tip 7 is formed by etching section 5. It should be possible to obtain a tip with a 1:3 or 1:4 diameter-to-length ratio and with a radius of about 10 mm at the apex 8.

Tip 7 is maintained at a constant distance of 10 nm above the surface of specimen 10. The diameter of the acoustic beam at the location of incidence will then also be in the 10 nanometer range, which will also be the resolution achievable with this instrument.

In order to obtain a reasonable signal-to-noise ratio, considering the inherent thermal noise, a primary acoustic power of 30 $\mu$W will be sufficient in either mode of operation.

When tip 7 is brought to within 10 to 15 nm from the surface of specimen 10, the reflected signal will have a certain amplitude, which is stored as a reference. As the acoustic beam is scanned across the specimen, the measured amplitude will vary in accordance with the topography of the surface and structural features of the specimen which lie within a zone below the surface of the specimen. The depth of this zone is determined by the penetration depth of the acoustic beam which, in turn, is a function of the frequency and power of the incident beam, as well as of the acoustic characteristics of the material of the specimen.

The transmission mode of operation may be used only where the thickness of specimen 10 is less than the penetration depth of the acoustic beam. The specimen is supported on a thin plastic film. Transducer 21 arranged on the rear side of specimen 10 detects the acoustic energy passing through specimen 10. As in the reflection mode, the amplitude of the output signal for each scanning point is correlated with the scanning coordinate information to generate an image of the specimen. The output signal is inherently ambiguous, since it contains information on the thickness of the specimen convolved with information on the material composition and structure of the specimen. It would be useful to have the output signals of both transducers, viz. transducer 11 for the reflection mode and transducer 21 for the transmission mode, processed by a suitable computer to obtain a consolidated image on the topography and on the internal structure of the specimen.

Having thus described our invention, what we claim as new, and desire to secure by Letters Patent is:

1. A scanning acoustic microscope, comprising:
    a coupling medium in which the specimen to be inspected is immersed;
    an acoustic lens formed in a solid body interfacing with said coupling medium, said lens having a focal point;
    at least one transducer element for transducing sound waves within said solid body; and
    means for raster-scanning said focal point of said lens across said specimen,
    and wherein said solid body comprises:
    a first section of a material having a first velocity of sound; and
    a second section of a material having a second velocity of sound lower than said first velocity of sound,
    said second section having an interface with said first section and a sharp tip opposite said interface,
    said first section having a free surface opposite said interface,
    one transducer of said at least one transducer element being mounted on said free surface of said first section of said solid body,
    said lens being formed by said interface,
    said focal point of said lens coinciding with the apex of said sharp tip,
    said tip being immersed in said coupling medium and being raster-scanned with respect to said specimen by said raster-scanning means.

2. A microscope in accordance with claim 1, wherein a second transducer of said at least one transducer element is positioned on the side of said specimen opposite said body.

3. A microscope in accordance with claim 1, wherein the materials of said first and second sections are chosen such that their respective acoustic impedances match each other in that the product of the sound velocity and density of the material of said first section is at least approximately equal to the product of the sound velocity and density of the material of said second section.

4. A microscope in accordance with claim 1, wherein said lens concavely extends within said first section and has a focal length on the order of 1 mm.

5. A microscope in accordance with claim 1, wherein said solid body has a diameter of about 1 mm, said lens has a diameter of between 50 $\mu$m and 600 $\mu$m, and the thicknesses of said first and second sections have approximately a 2:1 relationship.

6. A microscope in accordance with claim 1, wherein the relationship of the greatest diameter of said tip to its length is approximately 1:3 to about 1:4.

7. A microscope in accordance with claim 1, wherein said tip is has a sharp apex with a radius of approximately 10 nanometers.

8. A microscope in accordance with claim 1, wherein said apex is immersed in said coupling medium and said coupling medium has a relatively high absorption coefficient in the frequency range in which said at least one transducer element is operated.

9. A microscope in accordance with claim 8, wherein said coupling medium is selected from the group consisting of water, carbon tetrachloride and benzene.

10. A microscope in accordance with claim 1, wherein said first section consists of $Al_2O_3$ and said second section consists of a metal.

11. A scanning acoustic microscope, comprising:
    means for generating acoustic waves;
    a solid low-loss acoustic propagation medium for receiving said acoustic waves, said solid medium having a tip for launching said acoustic waves in a z direction;
    means for supporting a specimen surface perpendicular to said z direction and in close proximity to said tip, said specimen surface thereby receiving acoustic waves launched from said tip;
    means for scanning said tip across said specimen surface in x and y directions perpendicular to said z direction;
    a non-solid high-loss acoustic propagation medium between said tip and specimen for making the amplitude of launched acoustic waves received by said specimen surface sensitively dependent upon the z direction distance between said tip and specimen surface;

acoustic wave sensing means for detecting the amplitude of launched acoustic waves received by said specimen surface and passed on to said acoustic wave sensing means, said sensed amplitude being a function of said z direction distance between said tip and said specimen surface;

means for moving said tip in the z direction with respect to said specimen surface in response to said sensed amplitude so as to keep said sensed amplitude substantially constant during a scan; and means for displaying the z position of said tip relative to said specimen as a function of the x and y position of said tip, said display means thereby creating an acoustic image of said specimen.

* * * * *